United States Patent
Neisser-Svae et al.

(10) Patent No.: US 8,962,813 B2
(45) Date of Patent: Feb. 24, 2015

(54) PURIFICATION AND USE OF A FACTOR FOR SUPPORTING WOUND HEALING

(75) Inventors: Andrea Neisser-Svae, Mödling (AT); Stefan Winge, Arsta (SE); Anna Mjärdestam, Arsta (SE)

(73) Assignee: Octapharma AG, Lachen (CH)

( * ) Notice: Subject to any disclaimer, the term of this patent is extended or adjusted under 35 U.S.C. 154(b) by 902 days.

(21) Appl. No.: 12/162,107

(22) PCT Filed: Jan. 25, 2007

(86) PCT No.: PCT/EP2007/050714
§ 371 (c)(1),
(2), (4) Date: Apr. 13, 2009

(87) PCT Pub. No.: WO2007/085626
PCT Pub. Date: Aug. 2, 2007

(65) Prior Publication Data
US 2010/0261651 A9    Oct. 14, 2010

(30) Foreign Application Priority Data
Jan. 25, 2006    (EP) .................................... 06100819

(51) Int. Cl.
| | | |
|---|---|---|
| A23J 1/00 | (2006.01) |
| A61K 35/14 | (2006.01) |
| A61K 38/24 | (2006.01) |
| C07K 14/475 | (2006.01) |
| C07K 14/485 | (2006.01) |
| C07K 14/49 | (2006.01) |
| C07K 14/495 | (2006.01) |
| C07K 14/50 | (2006.01) |

(52) U.S. Cl.
CPC ........... C07K 14/4753 (2013.01); C07K 14/485 (2013.01); C07K 14/49 (2013.01); C07K 14/495 (2013.01); C07K 14/50 (2013.01)
USPC ........... 530/413; 530/412; 530/416; 530/380; 530/399

(58) Field of Classification Search
None
See application file for complete search history.

(56) References Cited

U.S. PATENT DOCUMENTS

| | | | |
|---|---|---|---|
| 4,673,733 A | | 6/1987 | Chandra et al. |
| 4,839,298 A | * | 6/1989 | Kay et al. ...................... 436/175 |
| 5,004,805 A | | 4/1991 | Ghoda et al. |
| 5,348,941 A | * | 9/1994 | Middaugh et al. ............. 514/9.1 |
| 6,333,309 B1 | * | 12/2001 | Higashio et al. ............. 514/21.1 |
| 6,451,978 B2 | | 9/2002 | Winge |
| 2001/0034053 A1 | | 10/2001 | Winge |
| 2002/0099174 A1 | | 7/2002 | Johnston et al. |
| 2007/0021342 A1 | * | 1/2007 | Breen et al. ...................... 514/12 |

FOREIGN PATENT DOCUMENTS

WO    WO 01/53328 A1    7/2001

OTHER PUBLICATIONS

Cellulose Phosphate, 2005. http://www.markson.com/lit/corp/cellulos.htm, downloaded Oct. 28, 2011.*
Stephens et al. 1987, PNAS 84:3886-3890.*
Jones et al. 2005. Immunology and Cell Biol. 83:106-118.*
Brown, K.J., and Parish, C.R., "Histidine-Rich Glycoprotein and Platelet Factor 4 Mask Heparan Sulfate Proteoglycans Recognized by Acidic and Basic Fibroblast Growth Factor," *Biochemistry* 33:13918-13927, American Chemical Society (1994).
Godha, E., et al., "Human Hepatocyte Growth Factor in Plasma from Patients with Fulminant Hepatic Failure," *Exp. Cell. Res.* 166:139-150, Academic Press (1986).
Gohda, E., et al., "Purification and Partial Characterization of Hepatocyte Growth Factor from Plasma of a Patient with Fulminant Hepatic Failure," *J. Clin. Invest.* 81:414-419, American Society for Clinical Investigation (1988).
Miller-Anderson, M., et al., "Purification of Antithrombin III by Affinity Chromatography," *Thromb. Res.* 5:439-452, Pergamon Press (1974).
Sakuragawa, N., at al., "Studies on the Purification and Characteristics of Histidine-Rich Glycoprotein," *Semin. Thromb. Hemost.* 11:384-386, Thieme (1985).
Yano, K., et al., "Natural hepatocyte growth factor (HGF) from human serum and a bound form of recombinant HGF with heparan sulfate are indistinguishable in their physicochemical properties," *Int. J. Biol. Macromol.* 23:227-235, Butterworth-Heinemann (1998).
Zarnegar, R., and Michalopoulos, G., "Purification and Biological Characterization of Human Hepatopoietin A, a Polypeptide Growth Factor for Hepatocytes," *Cancer Res.* 49:3314-3320, American Association for Cancer Research (1989).
Amersham, "HiTrap Heparin HP," available online at http://www.jp.amershambiosciences.com/catalog/pdf_attach/18113477AB.pdf (accessed Jun. 2002).
International Search Report for International Application PCT/EP2007/050714, mailed on May 8, 2007, European Patent Office, Rijswijk, Netherlands.

* cited by examiner

*Primary Examiner* — Shulamith H Shafer
(74) *Attorney, Agent, or Firm* — Sterne, Kessler, Goldstein & Fox P.L.L.C.

(57) ABSTRACT

A process for manufacturing of a composition containing a purified factor for supporting wound healing selected from the group consisting of Hepatocyte Growth Factor (HGF) platelet derived growth factor (PDGF), Epidermal growth factor (EGF), transforming growth factor alfa (TGF-α), Transforming growth factor beta (TGF-β), insulin like growth factor (IGF-I) and Fibroblast growth factor (FGF) from sources, such as blood, containing the factor for supporting wound healing, wherein the manufacturing process comprises purification steps which are performed in the presence of antithrombin III (AT-III).

18 Claims, No Drawings

PURIFICATION AND USE OF A FACTOR FOR SUPPORTING WOUND HEALING

This application is a U.S. National Stage of International Application No. PCT/EP2007/050714, filed Jan. 25, 2007, which claims the benefit of European Patent Application No. 06100819.9, filed Jan. 25, 2006.

The present invention relates to processes for the purification and use of a plasma derived factor for supporting wound healing. Particular aspects of the invention include purification and methods to protect the molecule from degradation both in vitro and in vivo.

BACKGROUND ART

Among others, HGF is a factor for supporting wound healing and is a protein expressed in the mesenchymal cells such as lung macrophages and fibroblasts, kupffer cells in the liver, and leukocytes. HGF is a cytokine, which is secreted at cell damage and appears to have an importance for the regeneration of certain organs and for the healing of wounds. Chemically HGF is a glycoprotein, which first is synthesized as a native (inactive) precursor. The precursor is cleaved to active HGF in the damaged organ via a particular activator. HGF and other factors bind to heparin, which seems to be important for the activation of HGF and the binding to its receptor. The receptor binding to HGF is c-MET. Since the c-MET receptor only is down regulated in damaged organs, it is only cells in these damaged organs that appear to respond to a HGF-receptor interaction. Examples of such factors in the growth factor family having heparin binding affinities which factors have an influence on the wound healing process, include by others Platelet derived growth factor (PDGF), Epidermal growth factor (EGF), Transforming growth factor alfa (TGF-α), Transforming growth factor beta (TGF-β), insulin like growth factor (IGF-I) and Fibroblast growth factor (FGF).

Antithrombin III (AT-III) is a plasma glycoprotein that inhibits serine proteases in the coagulation cascade and, thus, plays a major role in the regulation of blood clotting. AT-III is an inhibitor of Factors IXa, Xa, XI, XIIa, and thrombin. Thus, AT-III regulates clot formation in different stages of the coagulation cascade. A small decrease of AT-III content in the blood is associated with increased risk of thromboembolism. AT-III concentrates are used in the prophylaxis and treatment of thromboembolic disorders in patients with acquired or hereditary AT-III deficiency. In addition, it has been reported that AT-III is involved in many other biological responses, for example angiogenesis and inflammatory responses. The function of AT-III in these mechanisms is not yet fully understood.

Purification of AT-III with affinity chromatography, using heparin as the solid phase bound ligand, is known in the art. Miller-Andersson et al. (Thrombosis Research 5, 439-452, 1974) discloses the use of heparin-Sepharose to purify human AT-III. The entire procedure, which included ion exchange and gel filtration chromatography, provided a 34% yield.

Histidine-rich glycoprotein (HRGP) is a single-chained plasma protein originally isolated in 1972. The exact physiological function of HRGP is still unknown. Due to interaction with heparin, fibrinogen and fibrin, plasminogen and activated platelets, HRGP is considered to be a modulator of coagulation and fibrinolysis (Koide, T. In: Fibrinolysis: Current Prospects. Gaffney, P J (Ed.), John Libbey & Co., London 1988, p. 55-63). The polypeptide chain consists of 507 amino acid residues and contains regions that share homology with other plasma proteins, e.g. AT-III (Koide, T. et al. (1986) Biochemistry 25, 2220-2225).

DISCLOSURE OF THE INVENTION

The active form of the factor for supporting wound healing is degraded fast in vivo, especially in the area of wounds which has triggered coagulation and proteolytic system including proteases. During a purification process, it is also in vitro important to be able to inhibit the degradation of both the native and the active form of the factor for supporting wound healing. One of the factors, HGF, is known to be transported in blood as an inactive precursor and to be activated during injury by specific activators. By way of example, the inactive (denatured) form of HGF could be detected in small amounts in almost all of tested purification methods, whereas the activated and/or non-activated form was only found using the methods of the invention. Surprisingly it was found that the removal of proteases and/or precursor of proteases, in combination with co-purification of two stabilizers (AT-III and/or HRGP) of HGF, resulted in enriched and activated and/or non-activated form of HGF which easily acts or can be converted to its active form. Due to the fact that HGF normally circulates in its inactive precursor form in vivo, it is apparently so that a native and/or an active HGF medical product could significantly improve the treatment of a lot of dysfunctions in the body, especially where a local application is possible, for example during wound healing. This can also be expected for other growth factors with heparin binding properties like for example Platelet derived growth factor (PDGF), Epidermal growth factor (EGF), Transforming growth factor alfa (TGF-α), Transforming growth factor beta (TGF-β), insulin like growth factor (IGF-I) and Fibroblast growth factor (FGF) and the purification and use of these growth factors is also expected to be improved in the presence of; AT-III and HRGP.

Depending on use, the activated and/or non-activated form of the factor for supporting wound healing can be supplied with or without two specific stabilizers, AT-III and HRGP, which by others acts as an inhibitor of proteolytic degradation of the native and activated form of the factor for supporting wound healing, thus, increasing the efficacy and the half-life of the product. Depending on application, in some cases it may be advantageous to supply only either the activated or non-activated form of the factor for supporting wound healing to the patient and in other cases it may be advantageous to supply a mixture thereof, including the addition of the selected stabilisers AT-III and HRGP. This is due to how fast the factor for supporting wound healing molecule should act. It is obvious that this principle is also valid for other growth factors having heparin binding properties which has similarities with HGF, for example Platelet derived growth factor (PDGF), Epidermal growth factor (EGF), Transforming growth factor alfa (TGF-α), Transforming growth factor beta (TGF-β), insulin like growth factor (IGF-I) and Fibroblast growth factor (FGF).

The invention pertains a process for manufacturing of a purified factor for supporting wound healing containing composition from sources containing the factor for supporting wound healing, such as blood, wherein purification steps are performed in the presence of Antithrombin III (AT-III), Histidine-rich glycoprotein (HRGP) or combinations thereof. The factors for supporting wound healing are selected from the group consisting of Hepatocyte Growth Factor (HGF) Platelet derived growth factor (PDGF), Epidermal growth factor (EGF), Transforming growth factor alfa (TGF-α), Transforming growth factor beta (TGF-β), IGF-I and Fibroblast growth factor (FGF) from sources, such as blood, containing the factor for supporting wound healing, wherein the manufacturing process comprises purification steps which are performed in the presence of Antithrombin III (AT-III).

The process of the invention can be performed by the following steps:

(i) thawing frozen blood, eventually removing a precipitate and further processing a supernatant,
(ii) subjecting the supernatant to a contact with an anion exchange chromatography material in a buffer solution required for anion exchange chromatography the buffer having salt concentrations comparable to physiological conditions and a pH value at about neutral, whereas the main part of the proteins are unbound (including factors for supporting wound healing, AT-III, HRGP, albumin, IgG, Transferin, Haptoglobulin etc.) and specific, proteins and proteases binds to the anion resin (for example prothrombin, FX, FIX etc.),
(iii) separating off the anion exchange chromatography material obtaining a solution (including factors for supporting wound healing, AT-III, HRGP, albumin, IgG, Transferin, Haptoglobulin etc.),
(iv) contacting the solution with heparin-affinity chromatography material whereas the main part of the proteins are unbound (albumin, IgG, Transferin, Haptoglobulin etc.),
(v) separating off the solution and treating the heparin-affinity chromatography material with a desorption buffer having an ionic strength sufficient to allow to desorb the factor for supporting wound healing from the heparin-affinity chromatography material (optionally treating the heparin sepharose material with a washing buffer before desorption of the factors for supporting wound healing fraction, the washing solution having an increased ionic strength enough to desorb impurity proteins (for example heparin cofactor II etc) but not desorbing the factors for supporting wound healing fraction),
(vi) collecting the desorption buffer which contains the factor for supporting wound healing, AT-III and HRGP.

In a second alternative the process of the invention can be performed by employing the following steps:
(i) thawing frozen blood plasma, optionally removing a precipitate and further processing a supernatant;
(ii) adding an inorganic adsorbtion material, such as diatomaceous earth, silicagel, alumina and incubation for a sufficient time to bind unwanted material, for example FXII and prekallikrein activator etc.,
(iii) adding lower aliphatic alcohol; such as $C_1$-$C_4$ alcohol; to form Cohn Fraction I;
(iv) removing the precipitate, if any, and the inorganic adsorbtion material;
(v) processing the Cohn Fraction I supernatant through an affinity chromatography material whereby native/active factor for supporting wound healing, AT-III and HRGP (native/active factor for supporting wound healing, AT-III and HRGPP are hereafter referred to as HAH) are bound, while the main part of other plasma proteins (for example albumin, IgG, Transferin, Haptoglobulin etc.) remain unbound and are removed;
(vi) eluting and collecting the factor for supporting wound healing containing material from the affinity chromatography material (optionally treating the affinity resin with a washing buffer before desorption of the factors for supporting wound healing fraction, the washing solution having an increased ionic strength enough to desorb impurity proteins (for example heparin cofactor II etc) but not desorbing the factors for supporting wound healing fraction).

In a third alternative the process of the invention can be performed by employing the following steps:
(i) thawing frozen blood plasma, optionally removing a precipitate and further processing a supernatant;
(ii) subjecting the supernatant to a contact with an anion exchange chromatography material in a buffer solution required for anion exchange chromatography the buffer having salt concentrations comparable to physiological conditions and a pH value at about neutral, whereas the main part of the proteins are unbound (including the factor for supporting wound healing, AT-III, HRGP, albumin, IgG, Transferin, Haptoglobulin etc.) and specific, proteins and proteases binds to the anion resin (for example prothrombin, FX, FIX etc.),
(iii) separating off the anion exchange chromatography material obtaining a solution (including the factor for supporting wound healing, AT-III, HRGP, albumin, IgG, Transferin, Haptoglobulin etc.),
(iv) adding an inorganic adsorbtion material, such as diatomaceous earth, silicagel, alumina and incubation for a sufficient time to bind unwanted material, for example FXII and prekallekrein activator etc.,
(v) adding lower aliphatic alcohol; such as $C_1$-$C_4$ alcohol; to form Cohn Fraction I;
(vi) removing the precipitate, if any, and the inorganic absorption material;
(vii) processing the Cohn Fraction I supernatant through an affinity chromatography material whereby active factors for supporting wound healing, AT-III and HRGP (HAH) are bound, while the main part of other plasma proteins (for example albumin, IgG, Transferin, Haptoglobulin etc.) remain unbound and are removed;
(viii) eluting and collecting the factors for supporting wound healing containing material from the affinity chromatography material (optionally treating the affinity resin with a washing buffer before desorption of the factors for supporting wound healing fraction, the washing solution having an increased ionic strength enough to desorb impurity proteins but not desorbing the factors for supporting wound healing fraction).

In a fourth alternative the process of the invention can be performed by employing the following steps:
(i) thawing frozen blood plasma, optionally removing a precipitate and further processing a supernatant;
(ii) processing the supernatant through an affinity chromatography material whereby active factor for supporting wound healing, AT-III and HRGP (HAH) are bound, while the main part of other plasma proteins (for example albumin, IgG, Transferin, Haptoglobulin etc.) remain unbound and are removed;
(iii) eluting and collecting the factor for supporting wound healing containing material from the affinity chromatography material (optionally treating the affinity resin with a washing buffer before desorption of the factor for supporting wound healing fraction, the washing solution having an increased ionic strength enough to desorb impurity proteins (for example heparin cofactor II etc) but not desorbing the factors for supporting wound healing fraction).

In a particular embodiment of the invention, the process comprises a virus inactivation in particular after step (vi). The virus inactivation in this process stage is preferably a treatment with chemicals which are able to inactivate viruses. Such virus inactivation is described in more detail in EP-A-131740, the so-called solvent/detergent process. The disclosure of EP-A-131740 is incorporated by reference. After the virus inactivation step an anion exchange chromatography may be performed. It is also possible to perform a cation exchange chromatography, in particular after the anion exchange chromatography. In a further embodiment of the process of the invention a chromatography on cellulose phosphate is performed. A chromatography on cellulose phosphate may be advantageous because it is sufficient to perform only this chromatography. However, it may also be advantageous to employ the chromatography on cellulose phosphate together with the anion and/or cation exchange chromatography.

Typically, the fraction containing HGF is employed on the cellulose phosphate matrix in a buffer which allows HGF to be adsorbed on this cellulose phosphate material. The elution of the HGF is achieved typically with buffers having an ionic strength of ≥0.05 M sodium chloride or equivalence thereof.

According to the invention the collected fractions obtained in the alternatives are concentrated and/or diafiltrated to obtain a concentrate. The concentrate can optionally be further processed by contacting the concentrate with a cation-exchange material. The cation-exchange material is treated with a buffer having an ionic strength to elute a fraction A1 containing predominately (>90(%) AT-III and by treating the material subsequently with a buffer having higher ionic strength to elute predominately the factor for supporting wound healing and HRGP which is collected. The factor for supporting wound healing and HRGP containing fraction is concentrated or diafiltrated to obtain a fraction A2.

In the second alternative of the process of the invention wherein a precipitation buffer is added to the concentrate, a filtration is performed and the precipitate is treated with a buffer for recovering of the factor for supporting wound healing and AT-III.

The further purification of the resulting native factors for supporting wound healing concentrate, using a cation exchange resin wherein the native factor for supporting wound healing and HRGP binds to the resin, can be performed by employing at least one of the following steps:
 (i) the factors for supporting wound healing/HRGP fraction is eluted from the cation exchange resin with a buffer having a conductivity of 10 to 450 mS/cm at room temperature, more preferable 20-200 mS/cm, most preferable 30-100 mS/cm;
 (ii) pH during the chromatography is kept between 6-9, in particular 6.5-8 or 6.75-7.25;
 (iii) the charged groups of the resin are attached to the resin using slightly hydrophobic polymeric carbon chains consisting of from about 10 to about 100 monomer units.

In more detail the conditions for the second alternative of purification of the resulting factor for supporting wound healing concentrate, using a salting out step by which HRGP is precipitated, are comprising:
 (i) a salt according to Hofmeister series is used, preferably selected from the group consisting of sodium sulphate, sodium phosphate, sodium citrate, ammonium sulphate and combinations thereof;
 (ii) the salt concentration being selected in the range of 0.3-3 M, in particular 0.5-2 M or 0.75-1.5 M;
 (iii) the pH of the solution being selected in the range of 4-10, in particular 6-9 or 7-8;
 (iv) the resulting precipitation is removed by filtration or centrifugation.

In order to provide a commercially applicable factor for supporting wound healing fraction the resulting native factor for supporting wound healing concentrate is treated to reduce pathogens comprising at least one of the following methods:
 (i) virus inactivation with a solvent detergent solution
 (ii) virus inactivation using light (for example UVC) or radioactive treatment.
 (iii) virus inactivation using heat-treatment
 (iv) virus removal using virus filters Subject matter of the present invention is also a composition of matter obtainable according to the process of the invention, comprising the activated and/or non-activated form of the factor for supporting wound healing, the active form of the factor for supporting wound healing or combinations thereof.

In an embodiment of the invention, the composition contains the activated and/or non-activated form of the factor for supporting wound healing and AT-III to increase the stability of the factor for supporting wound healing in vivo and in vitro. In another embodiment, the composition of the invention contains the activated and/or non-activated form of the factor for supporting wound healing and HRGP has been included to increase the stability of the native factor for supporting wound healing in vivo and in vitro. In particular the factor for supporting wound healing is either fully activated or the factor for supporting wound healing is non-activated.

It may be advantageous to add stabilizers selected from the group consisting of saccharides and amino acids to the fractions containing the wound healing factor and HRGP. Typically, the stabilizers may be polyole, arginine, trehalose, lysin, mannitol or combinations thereof.

Subject matter of the invention is also a pharmaceutical composition comprising a composition of the invention.

The pharmaceutical composition of the invention can be present in an activated and/or non-activated form of the factor for supporting wound healing or combination thereof, which is preferably in liquid or freeze-dried form and typically locally applied, mixed in a gel, spray or similar with an approximately dosage regime between 1-10 ng factor for supporting wound healing/cm$^2$ wound/day. The composition can also potentially be administrated (dependent on application) using one or more of the following ways: intravenously, intramuscularly, subcutaneous, via inhalation, intrathecally or per rectally.

EXPERIMENTAL METHODS

Quantitative Determination of AT-III

Biological activity (IU/ml) of AT-III was determined as heparin cofactor activity by monitoring the cleavage of the chromogenic Substrate H-D-Phe-Pip-Arg-pNA•2 HCl (Chromogenix, Sweden) by thrombin in presence of heparin and AT-III. See Frantzen Handeland et al. (Scand. J. Haematol. 31, 427-436, 1983) and van Voorhuizen et al. (Thromb. Haemostas. 52(3), 350-353, 1984).

Total Protein

Total protein concentration was determined by absorption measurements at 280 nm ($A_{280}$)-Concentration (mg/ml) for AT-III Solutions was calculated using the coefficient of 6.4 IU/mg.

Specific activity (SA) of AT-III was defined as the ratio between heparin cofactor activity calculated as IU/ml and A 280.

Quantitative Determination of Histidine-Rich Glycoprotein

HRGP was quantified using rocket electrophoresis technique wherein the height of the "rocket" is proportional to the antigen concentration (Laurell, C-B, (1966) Analyt. Biochem. vol. 15, p. 45; and Laurell, C-B (1972) J. Clin. Lab. Invest. vol. 29, suppl. 124, p. 21). HRGP rabbit antibodies (Behringwerke) was included in a 1% Agarose A gel (Amersham Pharmacia Biotech). HRGP sample (5 µl) was applied to the gel, which was nm over night (150V, 1 V/cm). The resulting antibody-antigen complex was stained and compared to the Standard (human serum).

Isoelectric Focusing

Isoelectric focusing was carried out using the PhastSystem (Amersham Pharmacia Biotech) with precast gels, pI 3-9, according to the Phast manual Separation technique file No. 100. (picture enclosed).

Characterization of HGF

To confirm the availability of intact HGF with the multiple functions characteristic of this cytokine, Western blot analysis was performed. Therefore, an SDS-PAGE was carried out under reducing and non-reducing conditions. The proteins, electrophoretically transferred onto nitro-cellulose sheets, was incubated with a commercially available anti-human HGF IgG (R&D Systems, Inc.) and then with a commercially available conjugated second antibody (R&D Systems, Inc.), specific for the first. Visualization of the antigen (protein) was done by a colour reaction.

Quantitative Determination of HGF

A commercially available solid phase ELISA (R&D Systems, Inc.) that is designed to measure HGF levels in cell culture supernatants, serum, and plasma was used to determine relative mass values for natural HGF.

A monoclonal antibody specific for HGF is pre-coated onto a microplate. Standards and samples were pipetted into the wells and any HGF present was bound by the immobilized antibody. After washing away any unbound substances, an enzyme-linked polyclonal antibody specific for HGF was added to the wells. Following a wash to remove any unbound antibody-enzyme reagent, a substrate solution was added to the wells and colour develops in proportion to the amount of HGF bound in the initial step. After the colour development is stopped the optical density of each well was determined using a microplate reader set to 450 nm.

Biologic Activity of HGF

Biological activity was determined by using commercially available wound healing-, migration-, and proliferation assays. See B. Rafferty et al (J. Immunol. Methods 258 (2001) 1-11).

EXAMPLES

Example 1

Purification of native (active) HGF, stabilised with AT-III and HRPG, according to the invention.

Step 1

Pooled human fresh-frozen blood plasma from healthy donors (1,200 kg) was thawed at 0° C. and the resulting cryoprecipitate (comprising e.g. factor VIII and fibronectin) were removed through centrifugation. The precipitate is normally used for further purification of FVIII.

Step 2

The resulting cryosupernatant (from step 1) was processed through an anion exchange column (70 liter DEAE-Sepharose FF, Amersham Pharmacia Biotech) to bind vitamin K-dependent proteins (factor IX, factor X, factor II, Protein C, Protein S, etc.). The column was washed with a buffer containing 0.14 M sodium Chloride and 5 mM sodium phosphate pH 7.0. The unbound protein fraction (approximately 1,270 kg) was further processed to step 3, whereas the proteins bound to the column was further processed to purify FIX, thrombin etc.

Step 3

The unbound protein fraction from step 2, was further processed by addition of ethanol to a final concentration of 8% (v/v) to obtain Cohn Fraction I precipitate, comprising e.g. fibrinogen and lipoproteins (Cohn et al. (1946) J. Am. Chem. Soc. 68, 459-475). Before the addition of ethanol, 5.5 kg of diatomaceous earth material (Hyflow Super cel) was added to the solution. The precipitate and the diatomaceous earth material were removed by centrifugation.

Step 4

The Cohn Fraction I supernatant (approximately 1,400 kg) was pH-adjusted to pH 7.8 and thereafter processed through an affinity chromatography column (120 liter heparin-Sepharose FF, Amersham Pharmacia Biotech) whereby native (active) HGF, AT-III and HRGP (HAH) bound, while the main part of other plasma proteins (albumin, IgG etc.) passed through the column. The column was washed with 600 kg buffer (0.4 M sodium chloride and 0.01 M sodium phosphate, pH 7.8) to remove inactive forms of proteins, and the HAH fraction was eluted with 500 kg buffer (2.3 M NaCl and 0.01 M sodium phosphate, pH 7.8). The resulting HAH-eluate was concentrated and diafiltered against 0.05 M sodium phosphate, pH 7.5, using an ultrafiltration membrane (Biomax-10, Millipore). The obtained diafiltered HAH-concentrate was designated as UF1.

Example 2

Purification of native (activated and/or non-activated) HGF stabilised with AT-III and HRPG, according to the invention Step 1

Pooled human fresh-frozen blood plasma from healthy donors (1,200 kg) was thawed at 0° C. and the resulting cryoprecipitate (comprising e.g. factor VIII and fibronectin) were removed through centrifugation. The precipitation is normally used for further purification of FVIII.

Step 2

The cryosupernatant from step 1, was further processed by addition of ethanol to a final concentration of 8% (v/v) to obtain Cohn Fraction I precipitate, comprising e.g. fibrinogen and lipoproteins (Cohn et al. (1946) J. Am. Chem. Soc. 68, 459-475). Before the addition of ethanol, 5.5 kg of diatomaceous earth material (Hyflow Super cel) was added to the solution, the solution was stirred for 1-2 h. The precipitate and the diatomaceous earth material were removed by centrifugation.

Step 3

The Cohn Fraction I supernatant (approximately 1,400 kg) was pH-adjusted to pH 7.8 and thereafter processed through an affinity chromatography column (120 liter heparin-Sepharose FF, Amersham Pharmacia Biotech) whereby native (active) HGF, AT-III and HRGP (HAH) bound, while the main part of other plasma proteins (albumin, IgG etc.) passed through the column. The column was washed with 600 kg buffer (0.4 M sodium chloride and 0.01 M sodium phosphate, pH 7.8) to remove inactive forms of proteins, and the HAH fraction was eluted with 500 kg buffer (2.3 M NaCl and 0.01 M sodium phosphate, pH 7.8). The resulting HAH-eluate was concentrated and diafiltered against 0.05 M sodium phosphate, pH 7.5, using an ultrafiltration membrane (Biomax-10, Millipore). The obtained diafiltered concentrate was designated as UF1.

Example 3

Further Purification of Native HGF, to Remove AT-III

The process was carried out at room temperature (+22° C.). The concentrate UF1 from example 1 or 2 ($A_{280}$=23.6; FIG. 1, lane 1) was diluted 1+3 with distilled water. The diluted solution (2,050 g, conductivity 2.6 mS/cm) was processed through a column (Pharmacia Biotech Bioprocess Column, 15 cm diameter) filled with Fractogel® EMD $SO_3$-650 (M) cation-exchange chromatography media (1.7 l) equilibrated with 10 mM sodium citrate, pH 7.5, 2.6 mS/cm. The flow rate was 9 l/h. When the protein solution had been loaded on the column, the column was washed with 7 volumes of equilibration buffer. The material that did not adsorb to the column was mixed with the wash (14.6 kg, designated as "Fraction A1"; FIG. 1, lane 2). The more strongly adsorbed proteins were eluted from the column with 1.9 kg buffer (1 M NaCl/10 mM sodium citrate, pH 7.5, conductivity 106 mS/cm). The eluate (1.9 kg) was concentrated and diafiltered against 0.1 M sodium citrate/1% Saccharose, pH 7.0. The obtained "A2" contained active HGF and HRGP (Table I and FIG. 1, lane 3).

TABLE I

Separation of AT-III and HGF/HRGP fractions according to the invention

|  | $A_{280}$ | AT-III content (%) | Native HGF Present | HRGP (mg/ml) |
|---|---|---|---|---|
| UF1 (HAH) | 33 | >80 | + | N.D. |
| Fraction A1 (AT-III) | 4.5 | >95 | − | <0.01 |
| Fraction A2 (HGF + HRGP) | 16 | <1 | + | 4.2 |

Example 4

Further Purification of Native HGF, to Remove HRGP

To 490 g of UF 1 (produced according to example 2) was added a precipitation buffer comprising 532 g 0.05M sodium phosphate buffer pH 7.5, 372 g. of sodium citrate and 237 g of sucrose. The precipitation buffer was added to the UF 1 solution during 30 minutes. After stirring for 15 minutes the precipitation was removed using a 0.45-0.2 µm filter, the filter was washed with the following buffer to recover HGF and AT-III: 1,617 g of sodium citrate and 1,012 g of sucrose, was dissolved in 4,400 g of 0.05M sodium phosphate pH 7.5. The resulting filtrate was denoted filtrate (see Table II).

TABLE II

Separation of AT-III and HGF from HRGP fractions according to the invention

|  | Weight (gram) | $A_{280}$ | AT-III content (%) | Native HGF Present | HRGP (mg/ml) |
|---|---|---|---|---|---|
| UF1 | 490 | 18.6 | >80 | + | + |
| Filtrate | 3,620 | 2.2 | >95 | + | − |

Example 5

In order to investigate the importance of AT III and/or HRGP for the optimum HGF recovery, the following experiment was performed:
A. The flow-through fraction of the Heparin-Sepharose, as performed according to example 2 (steps 1-3), was used for further preparation. This fraction. devoid of HGF, active AT-III and HRGP, was then spiked with HGF, but not with AT-III or HRGP. After solvent detergent treatment (Octoxynol, TnBP), this solution was filtrated (filter with a pore size of 0.45 µm) and applied onto a Q-Sepharose XL column (anion exchange resin). After washing of the column with a solution of 20 mM Tris/HCl, pH 7.0, which also served to remove SD reagents, bound proteins were eluted with a Tris/HCl buffer, pH 7.0. containing 0.2 M NaCl. This eluate was applied onto a Fractogel EMD $SO_3$ column. After a washing step, elution was performed with a 10 mM sodium citrate solution, pH 5.5, and 1 M NaCl.
B. The purification procedure was performed identically to that described in A, while purified AT-III was added to the HGF-spiked solution.
Results:
Evaluation of the different fractions obtained from runs A and B showed that the step yields of both chromatographies were significantly higher in the eluates from run B as compared to those chromatographies performed in the absence of AT-III, particularly of the Fractogel EMD $SO_3$— chromatography. A HGF step yield at least double of that obtained in the absence of AT-III was obtained.
Notably, in the absence of AT-III, HGF was also detected in fractions other than the eluate, whereas no HGF was detectable in the column flow-through and wash fractions of process B. but concentrated in the eluate.
In conclusion, these results demonstrate that the presence of AT-III significantly supports the HGF step yield. in particular having addressed anion- and cationexchange chromatographies performed here.

Example 6

The Heparin-Sepharose column eluate and UF1 according to example 2, i.e. containing HGF, AT-III and HRGP, was SD treated according to example 5, filtered (0.45 µm) and applied onto a cellulose phosphate column, which was washed with 1 mM phosphate buffer, pH 6.0. Elution of HGF was performed with 1 M NaCl in phosphate buffer,
By this chromatography, the removal of SD reagents and a further purification of HGF was achieved with a process step yield of more than 50% of HGF as compared to the raw material.

The invention claimed is:
1. A method of purifying a factor for supporting wound healing selected from the group consisting of hepatocyte growth factor (HGF), platelet derived growth factor (PDGF), epidermal growth factor (EGF), transforming growth factor alpha (TGF-α), transforming growth factor beta (TGF-β), and insulin like growth factor (IGF-I) from a source containing said factor, wherein all purification steps of the method are performed in the presence of antithrombin III (AT-III) and the method comprises:
(i) thawing a frozen source containing the factor for supporting wound healing, removing a precipitate of the thawed source, and further processing a supernatant of the thawed source containing the factor for supporting wound healing;
(ii) contacting a solution containing the supernatant and AT-III with a heparin-affinity chromatography material;
(iii) separating the solution from the heparin-affinity chromatography material and contacting the heparin-affinity chromatography material with a desorption buffer having an ionic strength sufficient to desorb the factor for supporting wound healing from the heparin-affinity chromatography material; and

(iv) collecting the desorption buffer containing the factor for supporting wound healing, AT-III, and histidine-rich glycoprotein (HRGP).

2. The method of claim 1, comprising the following steps:
(i) thawing a frozen source containing the factor for supporting wound healing, wherein the frozen source is frozen blood, removing a precipitate of the thawed source, and further processing a supernatant of the thawed source containing the factor for supporting wound healing;
(ia) contacting the supernatant with an anion exchange chromatography material in a buffer solution required for anion exchange chromatography, wherein the buffer solution has salt concentrations comparable to physiological conditions and a pH value at about neutral;
(ib) separating the solution containing the factor for supporting wound healing and AT-III from the anion exchange chromatography material;
(ii) contacting the solution with a heparin-affinity chromatography material;
(iii) separating the solution from the heparin-affinity chromatography material with a desorption buffer having an ionic strength sufficient to desorb the factor for supporting wound healing from the heparin-affinity chromatography material; and
(iv) collecting the desorption buffer containing the factor for supporting wound healing, AT-III, and HRGP.

3. The method of claim 1, comprising:
(i) thawing a frozen source containing the factor for supporting wound healing, wherein the frozen source is frozen blood plasma, removing a precipitate of the thawed source, and further processing a supernatant of the thawed source containing the factor for supporting wound healing;
(ia) adding an inorganic adsorption material selected from the group consisting of diatomaceous earth, silica gel, and alumina; and incubating for a sufficient time to bind unwanted material;
(ib) adding a lower aliphatic alcohol comprising $C_1$-$C_4$ alcohol to form a Cohn Fraction I supernatant;
(ic) removing any precipitate and the inorganic adsorption material;
(ii) contacting the Cohn Fraction I supernatant, which is a solution containing the factor for supporting wound healing, AT-III, and HRGP, with a heparin-affinity chromatography material;
(iii) separating the solution from the heparin-affinity chromatography material and contacting the heparin-affinity chromatography material with a desorption buffer having an ionic strength sufficient to desorb the factor for supporting wound healing from the heparin-affinity chromatography material; and
(iv) collecting the desorption buffer containing the factor for supporting wound healing, AT-III, and HRGP.

4. The method of claim 1, comprising the following steps:
(i) thawing a frozen source containing the factor for supporting wound healing, wherein the frozen source is frozen blood plasma, removing a precipitate of the thawed source, and further processing a supernatant of the thawed source containing the factor for supporting wound healing;
(ia) contacting the supernatant with an anion exchange chromatography material in a buffer solution required for anion exchange chromatography, wherein the buffer solution has salt concentrations comparable to physiological conditions and a pH value at about neutral, wherein the factor for supporting wound healing, AT-III, and HRGP remain unbound, while other proteins comprising one or more of prothrombin, factor X, and factor IX bind to the anion exchange chromatography material;
(ib) separating the solution containing the factor for supporting wound healing and HRGP from the anion exchange chromatography material;
(ic) adding an inorganic adsorption material selected from the group consisting of diatomaceous earth, silica gel, and alumina; and incubating for a sufficient time to bind unwanted material comprising factor XII and/or prekallikrein activator;
(id) adding a lower aliphatic alcohol comprising $C_1$-$C_4$ alcohol to form a Cohn Fraction I supernatant;
(ie) removing any precipitate and the inorganic absorption material;
(ii) contacting the Cohn Fraction I supernatant, which is a solution containing the factor for supporting wound healing, AT-III, and HRGP, with a heparin-affinity chromatography material;
(iii) separating the solution from the heparin-affinity chromatography material and contacting the heparin-affinity chromatography material with a desorption buffer having an ionic strength sufficient to desorb the factor for supporting wound healing from the heparin-affinity chromatography material; and
(iv) collecting the desorption buffer containing the factor for supporting wound healing, AT-III, and HRGP.

5. The method of claim 1, comprising the following steps:
(i) thawing a frozen source containing the factor for supporting wound healing, wherein the frozen source is frozen blood plasma, removing a precipitate of the thawed source, and further processing a supernatant of the thawed source containing the factor for supporting wound healing;
(ii) contacting a solution containing the supernatant and AT-III with a heparin-affinity chromatography material;
(iii) separating the solution from the heparin-affinity chromatography material and contacting the heparin-affinity chromatography material with a desorption buffer having an ionic strength sufficient to desorb the factor for supporting wound healing from the heparin-affinity chromatography material; and
(iv) collecting the factor for supporting wound healing, AT-III, and HRGP.

6. The method according to any one of claims 1 to 5, wherein the collected factor for supporting wound healing is concentrated and/or diafiltrated to obtain a concentrate.

7. The method according to any one of claims 1 to 5 further comprising a virus inactivation step.

8. The method according to any one of claims 1 to 5 further comprising a cation exchange chromatography step.

9. The method according to any one of claims 1 to 5 further comprising a nanofiltration step.

10. The method of claim 7, wherein said virus inactivation step comprises using a virus-inactivating chemical.

11. The method of claim 10, wherein said material treated with virus inactivating chemicals is farther subjected to a cellulose phosphate chromatography step.

12. The method of claim 10, wherein said material treated with virus inactivating chemicals is subjected to anion exchange chromatography followed by cation exchange chromatography.

13. The method according to any one of claims 1 to 5, wherein a precipitation buffer is added to the collected factor for supporting wound healing to obtain a precipitate, the precipitate is then filtered and treated with a buffer to recover the factor for supporting wound healing and antithrombin III (AT-III).

14. The method according to any one of claims 1 to 5, wherein the factor for supporting wound healing is treated to reduce pathogens comprising at least one of the following methods:
   (i) virus inactivation with a solvent detergent solution;
   (ii) virus inactivation using ultra violet light or radioactive treatment;
   (iii) virus inactivation using heat-treatment; and
   (iv) virus removal using virus filters.

15. The method according to any one of claims 1 to 5, wherein the factor for supporting wound healing is further purified using a cation exchange resin, wherein the factor for supporting wound healing and histidine-rich glycoprotein (HRGP) binds to the resin comprising at least one of the following:
   (i) eluting the factor for supporting wound healing and HRGP fraction from the cation exchange resin with a buffer having a conductivity at room temperature selected from the group consisting of 10 to 450 mS/cm, 20-200 mS/cm, and 30-100 mS/cm;
   (ii) keeping the pH during the chromatography at a pH selected from the group consisting of pH 6-9, pH 6.5-8, and pH 6.75-7.25; and
   (iii) attaching the charged groups of the resin to the resin using slightly hydrophobic polymeric carbon chains comprising from about 10 to about 100 monomer units.

16. The method according to any of claims 1 to 5, wherein the factor for supporting wound healing is further purified using a salting out step by which histidine-rich glycoprotein (HRGP) is precipitated, wherein a salt according to Hofmeister series is used, selected from the group consisting of sodium sulphate, sodium phosphate, sodium citrate, ammonium sulphate and combinations thereof; wherein the salt concentration range is selected from the group consisting of 0.3-3 M, 0.5-2 M, and 0.75-1.5 M; wherein the pH range of the solution is selected from the group consisting of pH 4-10, pH 6-9, and pH 7-8; and wherein the resulting precipitate is removed by filtration or centrifugation.

17. The method of claim 8 wherein the cation-exchange material is treated with a buffer having an ionic strength to elute a fraction containing AT-III and subsequently treating the cation-exchange material with a buffer having higher ionic strength to elute the factor for supporting wound healing and HRGP which is collected.

18. The method of claim 17 wherein the factor for supporting wound healing and HRGP containing fraction is concentrated or diafiltrated.

* * * * *